United States Patent [19]
Tu et al.

[11] Patent Number: 6,050,993
[45] Date of Patent: Apr. 18, 2000

[54] MEDICAL DEVICE AND METHODS FOR TREATING HEMORRHOIDS

[75] Inventors: Lily Chen Tu; Hosheng Tu, both of Tustin, Calif.

[73] Assignee: Quantum Therapeutics Corp., Aliso Viejo, Calif.

[21] Appl. No.: 09/122,913

[22] Filed: Jul. 27, 1998

[51] Int. Cl.[7] .................................................. A61B 18/18
[52] U.S. Cl. .............................. 606/41; 606/42; 607/102
[58] Field of Search .......................... 606/41, 42, 45–50; 607/101, 102

[56] References Cited

U.S. PATENT DOCUMENTS

| | | | |
|---|---|---|---|
| 5,354,296 | 10/1994 | Turkel | 606/41 |
| 5,507,743 | 4/1996 | Edwards et al. | 606/41 |
| 5,569,245 | 10/1996 | Guglielmi et al. | 606/49 |
| 5,738,683 | 4/1998 | Osypka | 606/47 |
| 5,906,615 | 5/1999 | Thompson | 606/45 |
| 5,921,982 | 7/1999 | Lesh et al. | 606/41 |
| 5,980,519 | 11/1999 | Hahnen et al. | 606/49 |
| 5,980,563 | 11/1999 | Tu et al. | 607/113 |

*Primary Examiner*—Michael Peffley

[57] ABSTRACT

A medical device for treating the hemorrhoid, or reducing the dilatation of cellular tissues, wherein an elongate tubular shaft comprises at least one coil loop electrode means disposed at its distal end portion of the shaft, a RF energy generating means, and a means for pressing the electrode means against the target tissue to effect the ablation and the pressure therapy for the hemorrhoid tissues.

4 Claims, 6 Drawing Sheets

MEDICAL DEVICE AND METHODS FOR TREATING HEMORRHOIDS

The present invention generally relates to an improved medical device and methods for treating tissues, and more particularly, to such a medical device and methods for treating hemorrhoids and/or polyps in a patient by delivering RF energy to the lesion sites in association with a therapeutic pressure therapy.

BACKGROUND OF THE INVENTION

The method of reducing the size of cellular tissues in situ has been used in the treatment of many diseases, or as an adjunct to surgical removal procedures. One method used requires heating the tissues, and causing them to shrink and tighten. It is often less traumatic than surgical procedures and may be the only alternative method, wherein other procedures are unsafe or ineffective. Ablative treatment devices have an advantage because of the use of a destructive energy that is rapidly dissipated and reduced to a nondestructive level by conduction and convection, to forces of circulating fluids and other natural processes.

Devices using microwave energy, radiofrequency energy (RF), ultrasonic energy, cryogenic means, laser energy, and tissues destructive substances have been used to destroy malignant, benign, and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave energy antenna, through a duct, to the area of treatment, and applying energy diffusively through the duct wall into the surrounding tissues in the targeted directions.

Of particular interest to the present invention are RF therapeutic protocols, which have been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the device-to-tissues contact site to obtain the desired temperature for treating a tissue.

Hemorrhoid is a varicose dilatation of a vein of the superior or inferior hemorrhoidal plexus, resulting from a persistent increase in venous pressure. The external hemorrhoid is a varicose dilatation of a vein of the inferior hemorrhoidal plexus, situated distal to the pectinate line and covered with modified anal skin. The internal hemorrhoid is a varicose dilatation of a vein of the superior hemorrhoidal plexus, originating above the pectinate line, and covered by mucous membrane. A more serious case of hemorrhoid, prolapsed hemorrhoid, is an internal hemorrhoid that has descended below the pectinate line and protruded outside the anal sphincter. One of the worst cases, strangulated hemorrhoid, is an internal hemorrhoid which has been prolapsed sufficiently and for long enough time for its blood supply to become occluded by the constricting action of the anal sphincter.

Taylor in U.S. Pat. No. 5,578,047 teaches a hemorrhoid-removing device. Tuffel in U.S. Pat. No. 4,938,221 teaches a hemorrhoid inflammation-reducing device. Bidoia in U.S. Pat. No. 5,203,863 teaches an instrument for the ligation of hemorrhoids. None of them discloses a medical device by using a suitable energy to treat a dilated vein to shrink it. On the other hand, an alternative for hemorrhoid treatment is by surgically removing the dilated vein by a laser or other means. For a dilated vein, RF energy or other suitable energy can be applied for treating the tissues of the vascular walls, and causing them to shrink and tighten.

Imran in U.S. Pat. No. 5,281,218 entitled "Catheter having needle electrode for radiofrequency ablation" teaches a method using a needle electrode that is attached onto a catheter for radiofrequency ablation. Though a needle-like electrode is beneficial to ablate a tissue point for deep lesion, it is not disclosed that the particular needle electrode could possibly combine pressure therapy for proper contact with the target tissues. The "pressure therapy" is defined in this invention as application of an appropriate pressure onto the tissues by a medical device, in association with another therapy, such as a RF therapy.

Therefore, there is a need for an improved medical device and methods using the radiofrequency energy to treat a dilated vein or tissue, such as hemorrhoids while simultaneously applying pressure therapy to the target tissue.

SUMMARY OF THE INVENTION

In general, it is an object of the present invention to provide a method and an improved medical device for generating heat, to treat the hemorrhoids, vascular vessels, or other cellular tissues. It is another object of the present invention to provide a method and a device for monitoring the temperature of the medical device, and to control the temperature by utilizing a temperature control mechanism and/or algorithm. The location of the temperature sensor means is preferably at close proximity of the electrode means of the medical device. It is still another object of this invention to provide a method and a device for treating hemorrhoids, vascular walls, or cellular tissues in a patient by applying appropriate pressure to the tissues.

Briefly, heat is generated by supplying a suitable energy source to a device, which is comprised of at least one electrode means, in contact with the body tissues. A suitable energy source may consist of radiofrequency energy, microwave energy, ultrasonic energy, alternating current energy, or laser energy. The energy can be applied to the hemorrhoids, vascular walls, or cellular tissues through the electrode means. A DIP (dispersive indifferent pad) type pad or electrode, that contacts the patient, is connected to the Indifferent Electrode Connector on the RF generator. Therefore, the RF energy delivery becomes effective when a close circuit from a RF generator through a patient and returning to the RF generator is formed. When using an alternating current outlet, the generator should be grounded to avoid electrical interference. Heat is controlled by the power of the RF energy delivered and by the delivery duration. The standard RF energy generator means and its applications through the electrode means, to a patient are well known for those who are skilled in the art.

In an optional embodiment, means for generating vibration at the distal section comprises a motor mounted in the cavity of the handle, which has a rotatable motor shaft, an elongated connecting shaft having a first end, to which the distal end portion is connected, and a second end connected to the handle, a weight eccentrically mounted on the motor shaft with respect to the motor shaft axis, so as to rotate eccentrically, so that when the motor shaft rotates, the distal end portion of the device vibrates.

In one embodiment, the device comprises at least one electrode means, wherein the electrode means is composed of a compressible coil or plurality of coils. The coil is connected to an external RF generating means through an electrical conductor. The contact surface of the coil to the target tissue is pre-shaped and/or maximized by either flattening the contact surface or by pre-shaping the contact surface in a concave fashion to encircle the round surface of the hemorrhoids and the like. The coil is compressible so that when the coil electrode is pressed against the tissues or the round surface of a hemorrhoid, an appropriate pressure is exerted onto the tissues while applying the RF energy therapy.

The method and medical device of the present invention has several significant advantages over other known systems or techniques to treat the hemorrhoids or polyps. In particular, the device system comprising the electrode means, using RF energy as a heat source, in this invention and simultaneously applying pressure therapy to the tissues, results in a more efficient therapeutic effect, which is highly desirable in its intended application on the hemorrhoids or on other medical ablation applications.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
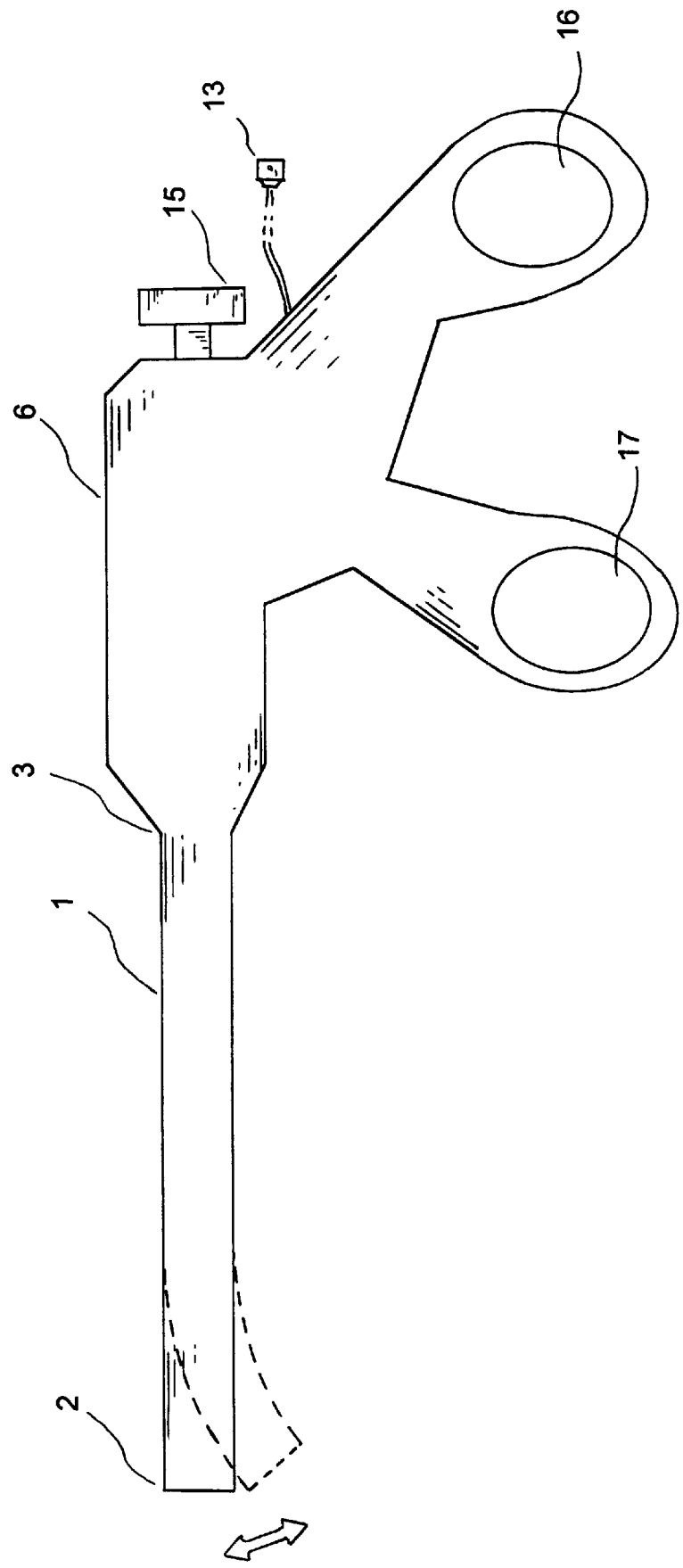
FIG. 1 is an over-all view of the medical device, comprising an electrode means having a compressible, flatten-top coil, constructed in accordance with the principles of the present invention.

Referring to FIGS. 1 to 6, what is shown is an embodiment of the medical device system, comprising simultaneously applying radiofrequency energy and applying a pressure therapy to treat the hemorrhoids, vascular walls, polyps, or other cellular tissues of a patient. As shown in FIG. 1, the medical device in the form of an elongate tubular assembly comprises a delivery tubular shaft 1 having a distal end 2, a proximal end 3, and at least one lumen 5 extending therebetween. A handle 6 is attached to the proximal end 3 of the delivery tubular shaft 1, wherein the handle 6 has a cavity 8. An inner elongate tubular shaft 11 is located within one lumen 5 of the delivery tubular shaft 1. In one embodiment, the delivery tubular shaft 1 and the accompanying inner elongate tubular shaft 11 are semi-flexible and bendable.

Figure 2:
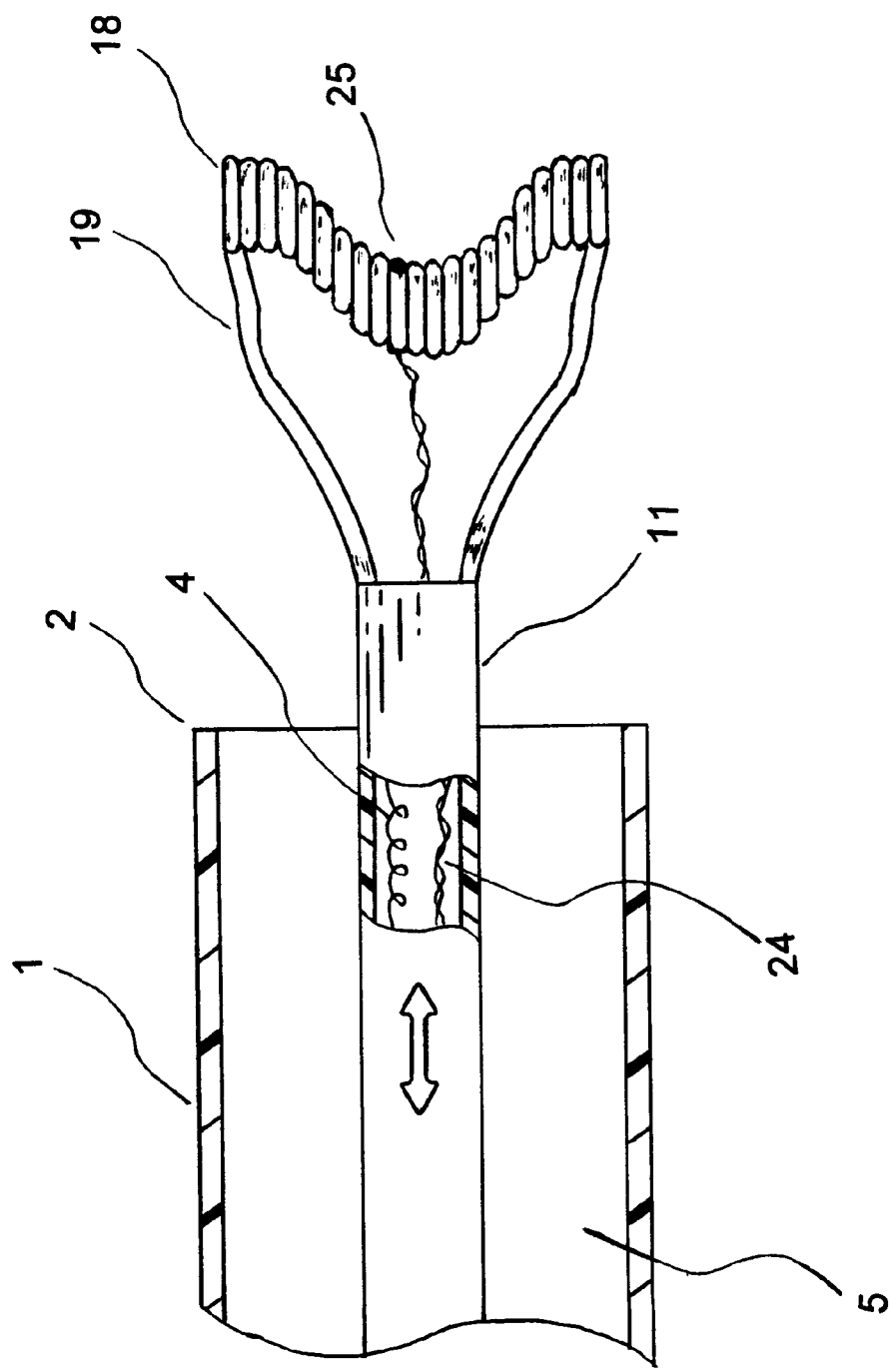
FIG. 2 is a cross-sectional view of the distal end portion of the device, including a flatten-top coil electrode for applying the pressure therapy to the medical device in FIG. 1.

FIG. 2 shows a cross-sectional view of the distal end portion of the device, including a flatten-top coil electrode 18 for applying the pressure therapy to the medical device. The inner elongate tubular shaft 11, on which thereof an electrode means 18, is mounted on a distal end portion 19, which surface is insulated. An insulated electrical conductor 4 passes through the shaft 11 and is connected to the electrode means 18, and mounted on a proximal end portion of the shaft to the handle 6 of the device.

Figure 3:
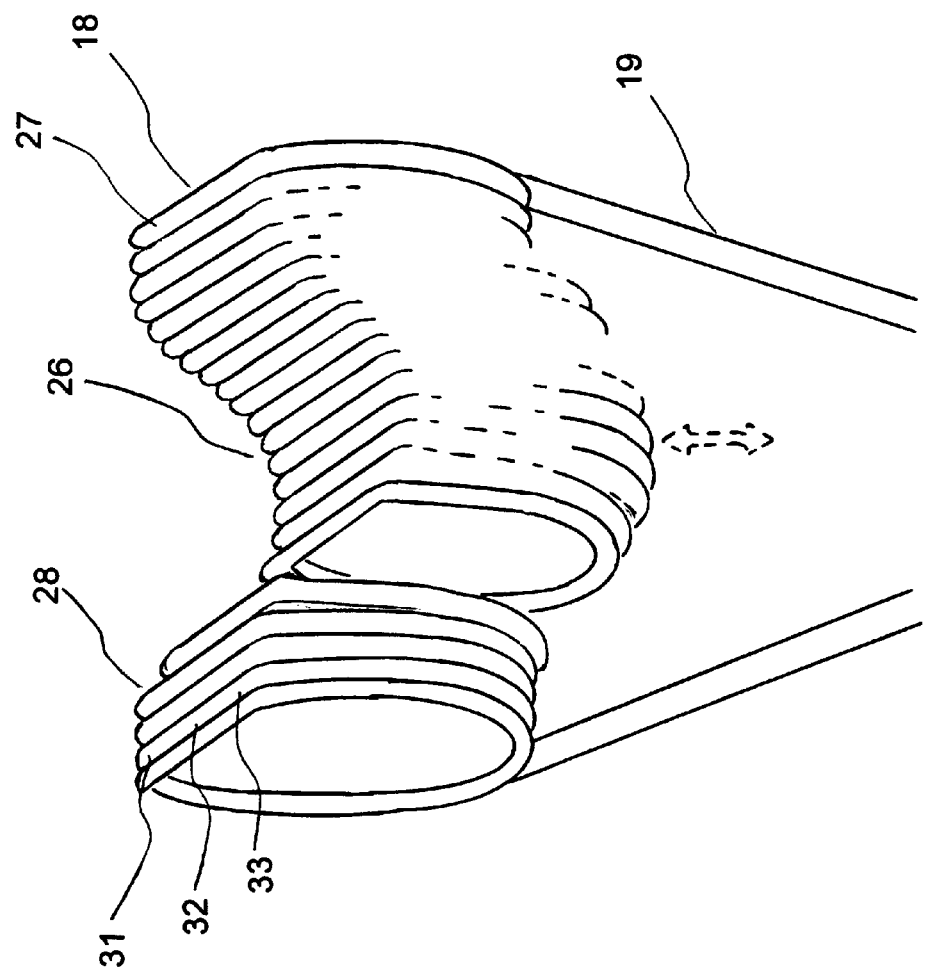
FIG. 3 is a perspective view of a compressible, flatten-top coil at the distal end of the medical device of the present invention.

FIG. 3 shows a perspective view of a compressible, flatten-top coil loop at the idistal end of the medical device. The electrode means 18 comprises at least one compressible coil loop having a distal end portion 26, 27, and 28 to contact a target tissue 47. The compressible coil loop has the capability of applying appropriate pressure to encircle and press the target tissue in the longitudinal direction along with the elongate tubular shaft 11. In one embodiment, the distal end portion of the compressible coil loop is shaped in a concave-top fashion relative to the target tissue and adapted to maximize the contact with the target tissue. This concave-top fashion is illustrated in FIG. 3 including the edge coils 27 and 28, and the center coil 26, which is at the bottom of the concave fashion. In another embodiment, the distal end portion of the compressible coil loop is shaped in a flatten-top fashion relative to the target tissue and adapted to maximize the contact with the target tissue. This flatten-top fashion is illustrated in FIG. 3, including the flat-top surface points 31, 32, and 33 on the same coil of the coil loop.

Figure 4:
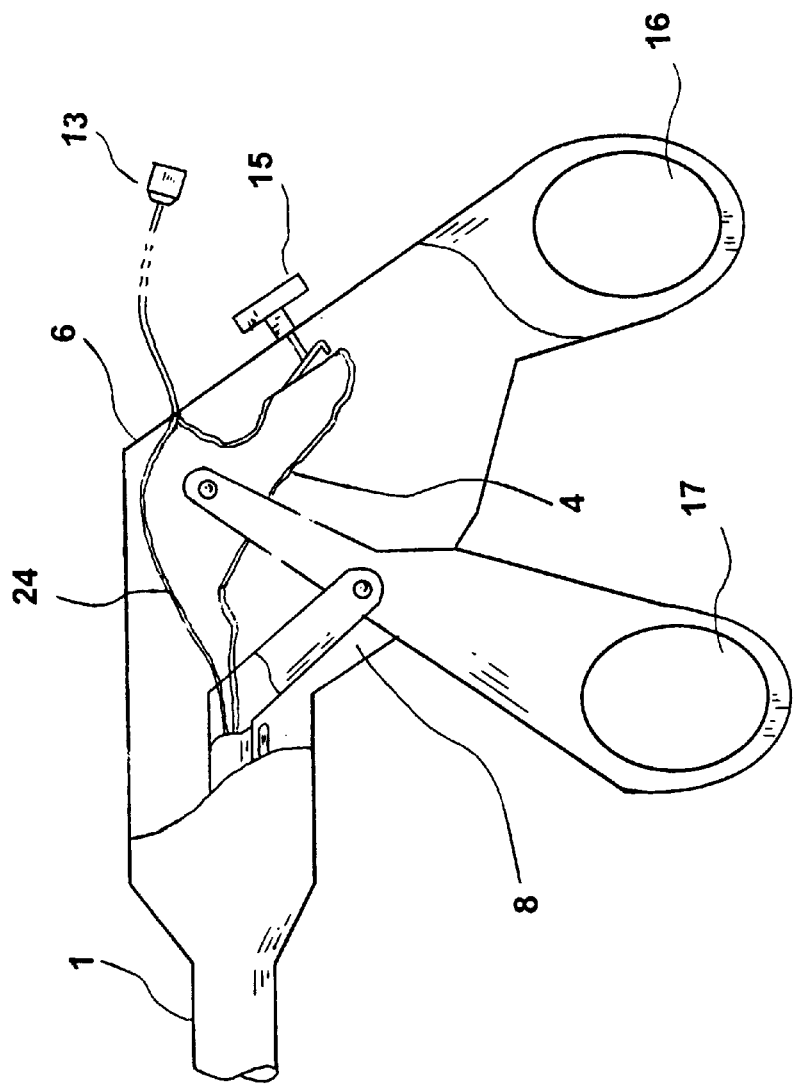
FIG. 4 is a cross-sectional view of the handle of FIG. 1.

FIG. 4 shows a cross-sectional view of the handle 6 of the present invention. The handle 6 comprises a cavity 8 and holders 16 and 17 for the thumb and finger so that the inner elongate tubular shaft 11 can be deployed with ease. The electricity of the electrical conductor 4 is controlled through an on-off control knob 15 to selectively deliver RF energy to the electrode means 18.

The device system comprises an external RF energy generating means (not shown), wherein the RF energy is provided to the electrode means 18 through the electrical conductor 4. A connector 13 is secured to the proximal end of the handle 6. The RF energy is supplied from an external RF energy generating means through an on-off knob 15 to control the RF energy delivery to the electrode means 18. The handle 6 has a thumb holder 16 and a finger holder 17 to guide the device to the appropriate location of the target tissue site. The finger holder 17 also serves as a delivery controller. The inner elongate tubular shaft 11 is deployed out of the delivery tubular shaft 1 and retracted to remain inside the delivery tubular shaft 1 by the control mechanism of the delivery controller 17.

The connector 13 comprises several pins for connecting an electrical conductor 4, and a temperature sensing wire 24 to external instruments, such as a RF generator, an EKG monitor, or a temperature control mechanism.

In one embodiment, at least one temperature sensing means 25 is disposed at close proximity of the electrode means 18. Insulated temperature sensor wire means 24 passes from the temperature sensing means 25 at the distal end portion, to an external temperature control mechanism through the outlet connector 13. The RF energy delivery is controlled by using the measured temperature from the temperature sensing means 25, through a closed-loop temperature control mechanism and/or algorithm. When the measured temperature rises to the preset high-limit point, the temperature control mechanism sends out a signal to cut off the RF energy supply. In a similar manner, when the measured temperature drops to the preset low-limit point, the temperature control mechanism sends out a signal to activate the RF energy supply.

Figure 5:
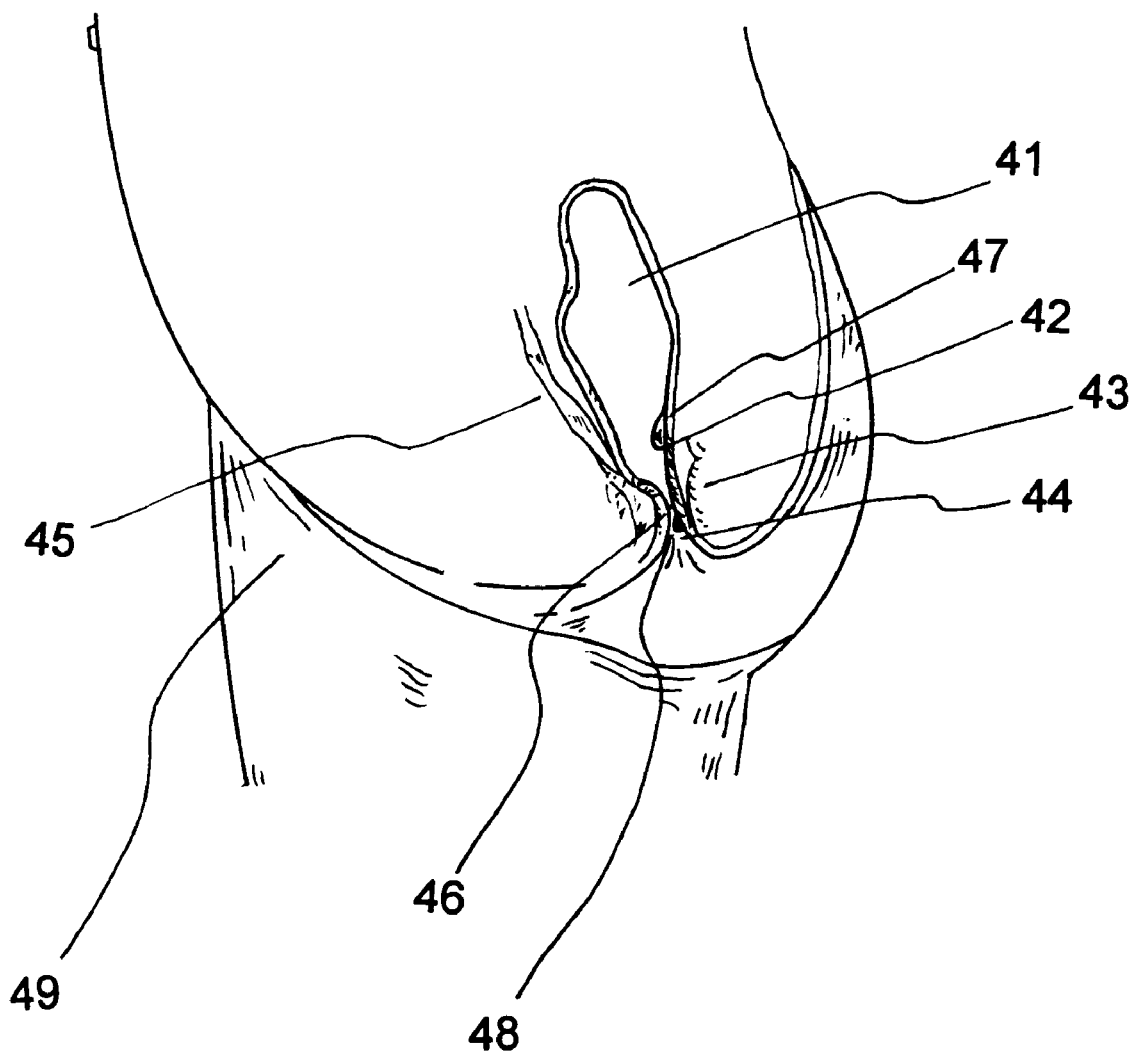
FIG. 5 is an illustrative side-view of the anal canal and hemorrhoids to be treated by the medical device of the present invention.

FIG. 5 shows a perspective view of a hemorrhoid region being treated by the medical device of the present invention. For illustrative purposes, the thigh 49 and the groin section of the body is shown in FIG. 5. The lower part of the rectum 41 is confined by sphincter ani internus 42 and sphincter ani externus 43. A pectinate line 46 separates the rectum 41 from the exterior portion of the body, wherein the opening for the rectum is the anal canal 44. An internal hemorrhoid 47 and an external hemorrhoid 48 are also shown to illustrate their relative anatomical location for ablation purposes.

During procedures, the medical device is inserted into the rectum through an anal canal 44. A method of treating a hemorrhoid of a patient, the method comprises: (a) placing a medical device system against the hemorrhoid of the patient, wherein the medical device comprises a delivery tubular shaft having a distal end, a proximal end, and at least one lumen extending therebetween, wherein the delivery tubular shaft is semi-flexible and bendable; a handle attached to the proximal end of the delivery tubular shaft, wherein the handle has a cavity; an inner elongate tubular shaft located within one lumen of the delivery tubular shaft, the inner elongate tubular shaft, on which, thereof an electrode means is mounted on a distal end portion, an electrical conductor passing through the shaft and connected to the electrode means, and mounted on a proximal end portion of the shaft to the handle of the device, wherein the electrode means comprises at least one compressible coil loop having a distal end portion to contact a target tissue; (b) applying an appropriate pressure on the at least one compressible coil loop to encircle and press the target tissue; and (c) applying RF energy to the tissues encircled under the exposed coil loop region to effect treatment of the hemorrhoid.

As an alternative illustration, A method of treating a hemorrhoid of a patient, the method comprising the steps of: (a) inserting a medical device through the anal canal into the rectum of a patient, wherein the medical device comprises an electrode means mounted on an elongate tubular shaft, wherein the elongate tubular shaft has a distal end, a proximal end, and a lumen extending therebetween, wherein the elongate tubular shaft is semi-flexible and bendable, a handle attached to the proximal end of the elongate tubular shaft, and an external RF generating means; (b) placing the electrode means of the medical device against and encircle the surface tissues of the hemorrhoid of a patient; (c) applying appropriate pressure through the electrode means upon the tissues of the hemorrhoid; and (d) applying RF energy to the tissues encircled under the electrode means of the medical device to effect treatment of the hemorrhoid tissues.

Figure 6:
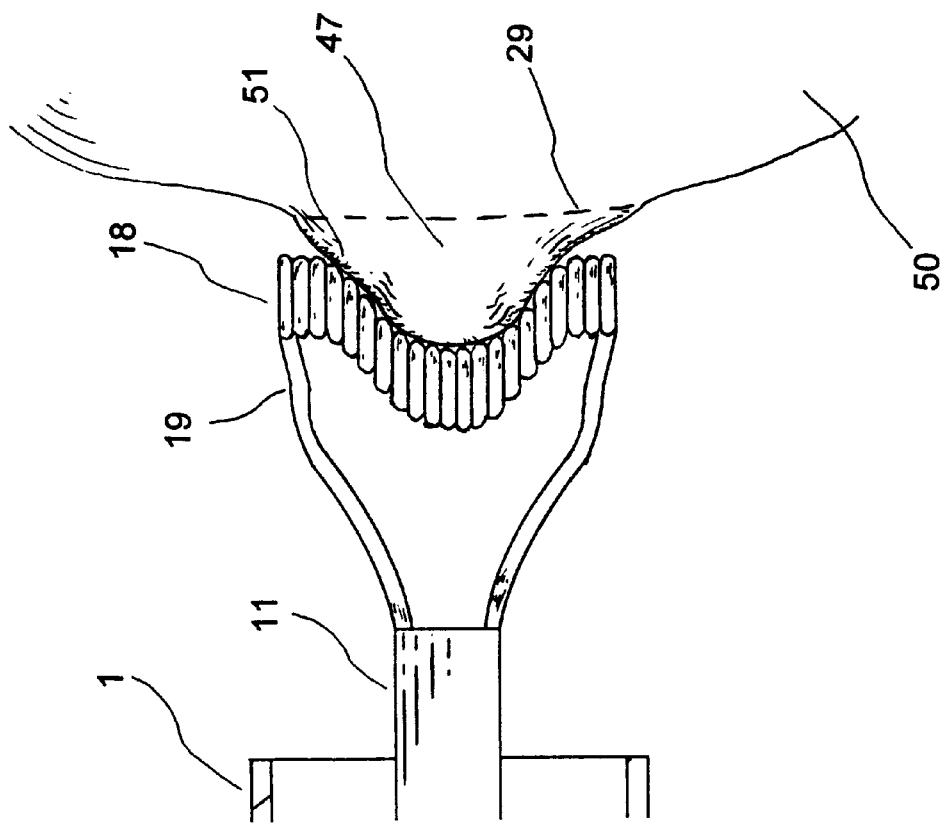
FIG. 6 shows a perspective view of a hemorrhoid region being treated by the medical device of the present invention.

FIG. 6 shows a perspective view of a hemorrhoid region being treated by the medical device of the present invention. The hemorrhoid 47 appears as a bump grown out of the tissue wall of the rectum 41. The hemorrhoidal bump 47 rises above the baseline 29 and forms a mound by an excessive internal venous pressure. The vessel wall 51 becomes dilated over a period of time, if not treated in time. The coil loop electrode 18 is in a concave fashion with its essential flatten-top encircling the dilated vessel wall 51. When simultaneously applying the pressure from the handle 6 and RF energy to the dilated vessel wall 51, the wall tissue contracts and tightens.

The external RF energy generator means has the capability to supply RF energy by controlling the time, power, and temperature through an optional separate closed-loop temperature control means. The patient is connected to the RF generator means through a DIP electrode to form a closed-loop current system. Therefore, RF energy is applied and delivered to the targeted hemorrhoid region, through the electrode means of this invention. The radiofrequency energy current in this invention is preferably within the range of 50 to 2,000 kHz. The frequency of the vibration of the medical device in this invention is preferably within the range of 60 to 1000 cycles per minute. By simultaneously applying RF energy to the electrode and by applying the pressure therapy, the hemorrhoid can be treated.

In a particular embodiment, the material for the electrode means of this invention consists of conductive metals such as platinum, iridium, gold, silver, stainless steel, Nitinol, or an alloy of these metals.

From the foregoing description, it should now be appreciated that a device system for the hemorrhoid and the treatment of vascular tissues, comprising a suitable energy source and a pressure therapy has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A medical device system comprising:

a delivery tubular shaft having a distal end, a proximal end, and at least one lumen extending therebetween;

a handle attached to the proximal end of the delivery tubular shaft, wherein the handle has a cavity;

an inner elongate tubular shaft located within one lumen of the delivery tubular shaft, the inner elongate tubular shaft, on which thereof an electrode means for treating tissue is mounted on a distal end portion, an electrical conductor passing through the inner elongate tubular shaft and connected to the electrode means, and mounted on a proximal end portion of the delivery tubular shaft to the handle of the device, wherein the electrode means comprises at least one compressible coil loop having a distal end portion to contact a target tissue, the compressible coil loop having the capability of applying appropriate pressure to encircle and press the target tissue, wherein the distal end portion of the compressible coil loop is shaped in a concave-top fashion relative to the target tissue and adapted to maximize contact with the target tissue; and a RF energy generating means, wherein the RF energy is provided to the electrode means through the electrical conductor.

2. The medical device system as in claim 1 further comprising at least one temperature sensor, wherein the temperature sensor is disposed at close proximity of the electrode means of the device system.

3. The medical device system as in claim 2 further comprising a temperature control means, wherein the temperature measured from the temperature sensor is relayed to the temperature control means and adapted to effect the RF energy supply to the medical device.

4. The medical device system of claim 1, wherein the RF energy is within the range of 50 to 2,000 kHz.

\* \* \* \* \*